United States Patent [19]

Kester et al.

[11] Patent Number: 4,855,308

[45] Date of Patent: Aug. 8, 1989

[54] METHOD OF TREATING SENILE COGNITIVE DECLINE WITH N'-SUBSTITUTED AMINOPYRIDINE ADRENERGIC AGENTS

[75] Inventors: Jeffrey A. Kester; Walter H. Moos; Anthony J. Thomas, all of Ann Arbor, Mich.

[73] Assignee: Warner-Lambert Company, Morris Plains, N.J.

[21] Appl. No.: 128,831

[22] Filed: Dec. 4, 1987

[51] Int. Cl.[4] .................... C07D 213/61; A61K 31/44
[52] U.S. Cl. .................................. 514/332; 514/352; 546/264; 546/304; 546/309; 546/312
[58] Field of Search ............... 546/264, 309, 304, 312; 514/332, 352

[56] References Cited

U.S. PATENT DOCUMENTS 3,450,707  6/1969  Bailey ................................. 260/296
3,624,096  11/1971  Abramovitch ................... 260/294.9
3,928,341  12/1975  Delarue ....................... 260/247.5 G
4,206,215  6/1980  Bailey ................................. 424/263
4,331,670  5/1982  Nishiyama ......................... 424/263

FOREIGN PATENT DOCUMENTS 0000816  2/1979  United Kingdom ............... 546/309

OTHER PUBLICATIONS

Hirota et al., *Bull. Soc. Chem. (Japan)*, 54:1583–1584.
Sammes, et al., *J. Med. Soc. Perkin Trans.* I, (1983), 973–978.

*Primary Examiner*—Mary C. Lee
*Assistant Examiner*—Zinna Northington
*Attorney, Agent, or Firm*—Ronald A. Daignault

[57] ABSTRACT

A method is disclosed for the treatment or amelioration of the symptoms of cerebral insufficiency characterized by decreased central adrenergic and/or cholinergic function employing certain N-substituted aminopyridines.

35 Claims, No Drawings

METHOD OF TREATING SENILE COGNITIVE DECLINE WITH N'-SUBSTITUTED AMINOPYRIDINE ADRENERGIC AGENTS

BACKGROUND OF THE INVENTION

The present invention relates to a medical method of treatment. More particularly, it concerns the use of certain N'-substituted aminopyridine compounds having adrenergic activity for ameliorating the symptoms of cognitive decline in the elderly.

U.S. Pat. No. 3,450,707 discloses 2-(3-fluoroanilino)-, and 2-(3-trifluoromethylanilino)pyridine and their N-oxides as antiinflammatory agents.

U.S. Pat. No. 3,624,096 discloses a process for preparing 2-aminopyridine compounds in which the amino group is substituted with phenyl, benzyl, p-tolyl, p-chlorophenyl, or p-nitrophenyl.

U.S. Pat. No. 3,928,341 discloses 4-[(2-chlorophenyl)amino]pyridine, 4-[(3-chlorophenyl)amino]pyridine, 4-[(3,5-dichlorophenyl)-amino]pyridine, 4-[(3-trifluoromethylphenyl)amino]pyridine, 4-[(2-methylphenyl)amino]pyridine, 4-[(2-ethylphenyl)amino]-pyridine, and 4-[(2,6-dimethylphenyl)amino]pyridine as intermediates for the preparation of certain N-aminoalkyl-4-anilino pyridines having central nervous system activity as excitants and antidepressants.

U.S. Pat. No. 4,206,215 discloses 4-[(4-chlorophenyl)amino]pyridine and 4-[(4-fluorophenyl)-amino]pyridine as intermediates for the preparation of bis-[4-[(substituted)amino]-1-pyridinium]alkanes having antimicrobial activity.

U.S. Pat. No. 4,331,670 discloses certain pyridylanilines having utility as agents for combatting insects, mites, fungi, or bacteria.

European patent application EP No. 0 000 816 to Baggaley discloses certain [[(substituted)phenyl]-amino]pyridines having hypoglycemic, hypolipidemic, and/or antilipolytic activity.

Hirota et al, *Bull. Soc. Chem. (Japan)*, 54: 1583-1584 discloses several 2-[[2-, 2-[[3-, and 2-[[(4-substituted)-phenyl]amino]pyridines in a study of the effect of substitution patterns on the N-H stretching frequency in the infrared spectrum of the compounds.

Sammes, et al, *J. Chem. Soc. Perkin Trans.* I, (1983), 973-978 discloses a synthetic route to several 4-[[2-, 4-[[3-, and 4-[[4-(substituted)phenyl]amino]-pyridines.

SUMMARY OF THE INVENTION

The present invention provides a method of treating the symptoms of senile cognitive decline in the elderly characterized by decreased cerebral adrenergic and cholinergic function. The treatment comprises administering to a patient an effective amount of a compound having the structure

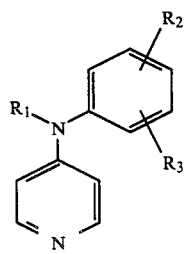

wherein $R_1$ is selected from hydrogen; alkyl of from one to six carbon atoms; alkanoyl of from two to six carbon atoms; benzoyl; carboxyl; carboxyalkyl; 2-, 3-, or 4-pyridinyl; phenyl; phenyl substituted with fluorine, chlorine, hydroxy, alkyl of from one to four carbon atoms, or alkoxy of from one to four carbon atoms; or phenylmethyl.

$R_2$ and $R_3$ are independently hydrogen; alkyl of from one to six carbon atoms; alkoxyl of from one to six carbon atoms; alkanoyl of from two to six carbon atoms; carboxyl; carboxyalkyl in which alkyl contains from one to six carbon atoms; halogen; hydroxy; cyano; trifluoromethyl; nitro; —$SO_3H$; amino; alkylamino, or dialkylamino in which alkyl contains from one to four carbon atoms.

DETAILED DESCRIPTION

Memory problems are perhaps the most conspicuous psychological problems of aging, ranging from persistent forgetfulness to clinical dementia. Age-associated memory impairment (AAMI) is characterized by a transient failure to recall details about recent events. Simple primary degenerative dementia (SPDD) is characterized by a profound loss of recent memory, relatively selective cholinergic deficit and late onset, generally after 65 years of age. Complex primary degenerative dementia (CPDD) is characterized by adrenergic and global cognitive deficits and early age of onset.

Together, AAMI, SPDD, and CPD represent a large percentage of senile cognitive decline (SCD), which is defined as the variety of cognitive disorders that accompany aging, constituting a major and growing public health problem. Presently, 5-10% of the population at 65 years of age and up to 20% of the population over 80 years of age are affected.

While cholinergic dysfunction contributes in part to SCD, other neutrotransmitter systems are clearly involved. Consistent reductions in noradrenergic function arising from neuropathological abnormalities in noradrenergic containing cell bodies in the locus coeruleus accompany SCD. This results in decreases in the levels of norepinephrine and numbers of $\alpha$ adrenergic receptors in the cerebral cortex and basal forebrain of aged humans and patients with dementia.

Agents which increase central noradrenergic function ameliorate these neurochemical abnormalities and are useful in the treatment of SCD. Thus, $\alpha 2$-adrenergic antagonists, which increase the availability of norepinephrine, represent potentially effective therapy for SCD. In addition, agent which increase central noradrenergic function may also indirectly activate cholinergic function.

Cognitive deficits are not restricted to the aged. These deficits are found at all ages and in a variety of clinical situations, including head trauma, hypoxic and pharmacologic insult, convulsive disorders, mental retardation, and learning disorders. An agent which enhances central adrenergic and/or cholinergic function may also be useful in treating cognitive dysfunction associated with these disorders.

The compounds in the present invention are selective $\alpha 2$ antagonists, with additional effects on the cholinergic system, and are thus effective in the treatment or amelioration of cognitive dysfunction. The compounds in this invention are 4-aminopyridines in which the 4-amino group may be monosubstituted (i.e., a secondary amine) or disubstituted (i.e., a tertiary amine). The preferred secondary amines are N-((substituted)- phenyl)-4-pyridinamines in which the phenyl group may be mono-, or disubstituted with alkyl of from one to six carbon atoms; alkoxyl of from one to six carbon atoms; alkanoyl of from two to six carbon atoms; carboxyl; carboxyalkyl in which alkyl contains from one to six carbon atoms; halogen; hydroxy; cyano; trifluoromethyl; nitro; —SO$_3$H; amino; alkylamino or dialkylamino in which alkyl contains from one to four carbon atoms.

The tertiary amines are substituted on the 4-amino nitrogen atom as described just above, with the 4-amino nitrogen atom additionally bearing a substituent selected from alkyl of from one to six carbon atoms; alkanoyl of from two to six carbon atoms; benzoyl; carboxyl; carboalkoxy; 2-, 3-, or 4-pyridinyl; (substituted)-phenyl; or phenylmethyl.

The term "alkyl of from one to six carbon atoms" denotes a substituent group derived from a saturated hydrocarbon by removal of a single hydrogen atom. The term includes methyl, ethyl, n-propyl, iso-propyl, n-butyl, sec-butyl, iso-butyl, tert-butyl, and the various isomeric forms of pentyl and hexyl.

The term "alkoxy" denotes a substituent group derived by removal of the hydrogen from the oxygen atom of a saturated alcohol and attached to the parent molecular moiety through the oxygen atom. Such groups include methoxyl, ethoxyl, 1- and 2-propoxyl, and similar branched and unbranched alkoxy groups of up to four carbon atoms.

The term "alkanonyl" denotes an alkyl group as previously defined, attached to the parent molecular moiety through a carbonyl group.

The term "carboxyl" denotes the acidic functional group —COOH, while carboxyalkyl denotes the ester function —COO—alkyl where alkyl is as previously defined.

Examples of compounds contemplated as falling within the scope of the present invention include, but are not limited to the following:
N-Phenyl-4-pyridinamine.
N-(3-Methylphenyl)-4-pyridinamine.
N-(4-Methylphenyl)-4-pyridinamine.
N-(4-Methyl-2-nitrophenyl)-4-pyridinamine.
N-(3-Methoxyphenyl)-4-pyridinamine.
N-(4-Methoxyphenyl)-4-pyridinamine.
N-(3,4-Dimethoxyphenyl)-4-pyridinamine.
N-(2-Chlorophenyl)-4-pyridinamine.
N-(3-Chlorophenyl)-4-pyridinamine.
N-(4-Chlorophenyl)-4-pyridinamine.
N-(3-Chlorophenyl)-N-methyl-4-pyridinamine.
N-(4-Chlorophenyl)-N-methyl-4-pyridinamine.
N-(2,4-Dichlorophenyl)-4-pyridinamine.
N-(3,4-Dichlorophenyl)-4-pyridinamine.
N-(4-Chloro-3-nitrophenyl)-4-pyridinamine.
N-(2-Nitrophenyl)-4-pyridinamine.
N-(3-Nitrophenyl)-4-pyridinamine.
N-4-Pyridinyl-1,2-benzenediamine.
N-4-Pyridinyl-1,3-benzenediamine.
N,N-Dimethyl-N'-4-pyridinyl-1,3-benzene-diamine.
N-[3-(Trifluoromethyl)phenyl]-4-pyridin-amine.
N-[4-(Trifluoromethyl)phenyl]-4-pyridin-amine.
3-(4-Pyridinylamiino)-benzonitrile.
3-(4-Pyridinylamino)benzoic acid, methyl ester.
3-(4-Pyridinylamino)benzoic acid, ethyl ester.
3-(4-Pyridinylamino)benzenesulfonic acid.
N-(3,4-Dichlorophenyl)-N-4-pyridinyl-4-pyridinamine.
N-(3,4-Dichlorophenyl)-N-4-pyridinylacet-amide.
N-(4-Methylphenyl)-N-4-pyridinylacetamide.
N-(3,4-Dichlorophenyl)-N-4-pyridinylbenz-amide.
(3,4-Dichlorophenyl)-4-pyridinylcarbamic acid, methyl ester.
(4-Methylphenyl)-4-pyridinylcarbamic acid, methyl ester.

Compounds of the present invention are prepared by one of the following general synthetic methods, A or B.

In Method A, N-(4-pyridyl)pyridinium chloride hydrochloride is heated to a temperature of about 150° C. with the desired aniline. Pyridine is distilled from the reaction mixture, and the crude product is further purified, if needed, by recrystallization. This method is exemplified by the production of N-(4-methoxyphenyl)-4-pyridinamine, Example 1, below.

In Method B, 4-chloropyridine hydrochloride is reacted in glacial acetic acid at about 100° C. for a period of from about six to ten hours with an approximately equimolar amount of the desired aniline. The crude product is isolated as the hydrochloride salt which is purified by recrystallization or which can be converted to the free base and purified. This method is exemplified by Examples 2-5 below.

The compounds of the present invention form pharmaceutically acceptable acid addition salts with organic and inorganic acids. Examples of suitable acids for the formation of pharmaceutically acceptable salts are hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane- and ethanesulfonic, hydroxymethane- and hydroxyethanesulfonic, and the like. (See for example, "Pharmaceutical Salts,"*J. Pharm. Sci.* 66(1): 1–19 (1977)).

The salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases, as sodium hydroxide, potassium carbonate, ammonia, and sodium bicarbonate may be utilized for this purpose.

The free base forms of the compounds of this invention differ somewhat from their respective salt forms in such physical properties as melting point and solubility in polar solvents, but the salts are otewise equivalent to their respective free acid or base forms for the purpose of the invention.

The biological activity of compounds of the present invention was evaluated using the "scopolamine induced swimming test" (SIS). This screen evaluated the ability of the test compounds to reverse the hyperactive swimming behavior of laboratory rats given scopolamine. in this test, untreated rats will generally swim between 20 to 30 meters during a five-minute test period. Rats given scopolamine at doses of 0.1 mg/kg develop a stereotypical swimming hyperactivity with the swimming distances generally increasing by 75–125% above baseline values. This increase in swimming hyperactivity can be reversed by administration of the acetylcholinesterase inhibitor physostigmine of the cholinergic agonist, arecoline. The effect of scopolamine on swimming behavior was determined to be centrally mediated since (1) the quaternary amine of scopolamine, scopolamine methyl nitrate, does not produce any behavioral changes under the same conditions, and (2) neostigmine, a quaternary amine analog of physostigmine, does not reverse the effect of scopolamine. We have discovered unexpectedly that α2-adrenergic antagonists including the compounds in this application also reverse this swimming hyperactivity, perhaps through indirect stimulation of the cholinergic system.

SIS values are reported as the percent reversal of scopolamine, and are determined as follows:

$$\% \text{ Reversal} = \frac{U - SDT}{U - ST} \times 100$$

where U, SDT, and ST represent, respectively, the mean activity level in meters swum of untreated, scopolamine-and-drug-treated, and scopolamine-treated mice. Representative results are presented in Table 1.

TABLE 1

Reversal of Scopolamine-Induced Swimming Hyperactivity

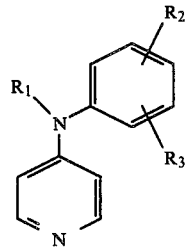

| Compound | $R_1$ | $R_2$ | $R_3$ | Percent Reversal Swimming Hyperactivity Dose (mg/kg, SC) | | |
|---|---|---|---|---|---|---|
| | | | | 0.32 | 3.2 | 32 |
| 1 | H | H | H | 27 | 22 | 57 |
| 2 | H | H | 3-CH$_3$ | 52 | 36 | 66 |
| 3 | H | H | 4-CH$_3$ | 10 | 25 | 100 |
| 4 | H | H | 3-Cl | 0 | 27 | 75 |
| 5 | H | H | 3-CF$_3$ | 0 | 0 | 57 |
| 6 | H | H | 4-CF$_3$ | 0 | 16 | 55 |
| 7 | H | H | 3-OCH$_3$ | 23 | 62 | 31 |
| 8 | H | H | 3-NO$_2$ | 40 | 39 | 70 |
| 9 | H | H | 2-NH$_2$ | 15 | 18 | 72 |
| 10 | H | H | 3-NH$_2$ | 47 | 0 | 41 |
| 11 | H | H | 3-N(CH$_3$)$_2$ | 15 | 4 | 61 |
| 12 | H | H | 3-COOCH$_3$ | 15 | 0 | 8 |
| 13 | H | 2-Cl | 4-Cl | 0 | 24 | 0 |
| 14 | H | 3-Cl | 4-Cl | 31 | 37 | 64 |
| 15 | H | 3-NO$_2$ | 4-Cl | 26 | 0 | 0 |
| 16 | H | 2-NO$_2$ | 4-CH$_3$ | 0 | 3 | 14 |
| 17 | Ac | H | 4-CH$_3$ | 35 | 56 | 21 |
| 18 | Ac | 3-Cl | 4-Cl | 33 | 34 | 30 |
| 19 | COOCH$_3$ | H | 4-CH$_3$ | 36 | 20 | 17 |
| 20 | COOCH$_3$ | 3-Cl | 4-Cl | 6 | 0 | 9 |

The compounds of the present invention also demonstrate selective antagonism at the α2-adrenergic binding site in the brain. The α2 binding sites are presynaptic and are involved in the control of release of norepinephrine. A compound which acts selectively as an α2-adrenergic antagonist acts to increase noradrenergic activity. Such increases in noradrenergic activity are related to improved cognitive function in animals.

The binding of representative compounds of this invention at the α1-adrenergic binding site was measured using the protocol described by Hornung, R., et al, Archiv. Pharm., 308:223 (1979). Similarly, the binding at the α2:adrenergic binding site was measured using the method of Rouot, B. R., et al, Life Sci., 25: 769 (1979). The data are presented in Table 2 and illustrate the α2 selectivity of the compounds.

TABLE 2

Selective Binding at the α1- and α2-Adrenergic Binding Sites

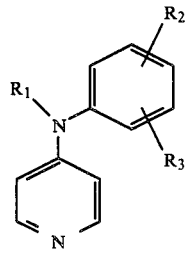

| Compound | $R_1$ | $R_2$ | $R_3$ | IC$_{50}$ (Nanomolar) | | |
|---|---|---|---|---|---|---|
| | | | | α1 | α2 | α1/α2 |
| 3 | H | H | 4-CH$_3$ | 1600 | 37 | 43 |
| 4 | H | H | 3-Cl | 7500 | 133 | 56 |
| 14 | H | 3-Cl | 4-Cl | >1000 | 118 | >8.5 |
| 17 | Ac | H | 4-CH$_3$ | >10000 | 5400 | >1.9 |

As seen from the data in Table 2, Compound 4 demonstrates a high degree of selectivity for binding at the α2-adrenergic site. This compound was tested in the Mouse Water Maze (MWM) test which is a direct test of spatial cognitive skill in laboratory mice. This test, which is described in Morris, R., J. Neurosci. Meth., 11: 47–60 (1984), measures the effect of a test drug on spatial working memory in hippocamally-deficient mice. In this test, Compound 4 demonstrated a minimal effective dose (MED) of 3.2 mg/kg.

In therapeutic use as agents for treating cerebral insufficiency, the compounds utilized in the pharmaceutical method of this invention are administered to the patient at dosage levels of from 0.001 mg to 100 mg per day. The specific dosages employed, however, may be varied depending upon the requirement of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting was such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorable, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following preparative examples are provided to enable one skilled in the art to practice the invention. They are illustrative of the present invention and are not to be read as limiting the scope of the invention as it is defined by the appended claims.

EXAMPLE 1

Preparation of N-(4-methoxyphenyl)-4-pyridinamine

A mixture of 1-(4-pyridinium chloride hydrochloride (10.0 g, 0.04 mol) and p-anisidine (4.9 g, 0.04 mol) is heated at 150° C. until the pyridine stops distilling. The resulting black oil is allowed to cool to room temperature during which time it solidifies. The solid is broken into a powder and repeatedly washed with acetone until the color is light brown. Recrystallization from isopropanol gives the product as a yellow powder, mp 129°–134° C.

EXAMPLE 2

Preparation of N-(3,4-dichlorophenyl)-4-pyridinamine

4-Chloropyridine hydrochloride (15.0 g, 0.10 mol) is dissolved in glacial acetic acid (150 ml) and 3,4-dichloroanailine (16.2 g, 0.10 mol) is added. The solution is heated to 100° C. for a period of eight hours. After cooling the solution to room temperature, the acetic acid is remove under vacuum to give the crude product as an off-white solid. The solid is washed with acetone and collected by filtration. Recrystallization from isopropanol yields N-(3,4-dichlorophenyl)-4-pyridinamine as the hydrochloride salt, as an offwhite powder, mp 240°–241° C.

EXAMPLE 3

Preparation of N-(3-chlorophenyl)-4-pyridinamine

3-Chloroaniline (12.8 g, 0.10 mol) is added to a solution of 4-chloropyridine hydrochloride (15.0 g, 0110 mol) in 150 ml of glacial acetic acid. The resulting solution is heated at 100° C. for eight hours. After cooling the mixture to room temperature, the acetic acid is removed under vacuum. The resulting solid is triturated with acetone, collected by filtration, and washed with diethyl ether.

Water (100 ml) is added to the pale yellow solid, and the undissolved material is filtered off. The aqueous layer is made basic with 6M sodium hydroxide solution and the solid which forms is collected by filtration and washed with acetone and then with diethyl ether.

The solid product is dried under vacuum at 100° C. for eight hours to produce an off-white solid, mp 123°–125° C.

EXAMPLE 4

Preparation of 3-(4-pyridinylamino)benzoic acid, methyl ester

3-Aminobenzoic acid, methyl ester (15.2 g, 0.10 mol) is added to a solution of 4-chloropyridine hydrochloride (15.0 g, 0.10 mol) in 150 ml of glacial acetic acid. The resulting mixture is heated to 100° C. for six hours and then cooled to room temperature.

The acetic acid is removed under vacuum to yield the crude product as an orange oil. The oil is taken up in 150 ml of water and the resulting solution is made basic with 6M sodium hydroxide solution. The aqueous solution is extracted three times with 100-ml portions of chloroform and the organic extracts are combined and dried over anhydrous magnesium sulfate. The chloroform is removed under vacuum to give the crude product, which is purified by recrystallization from ethyl acetate to yield a pale yellow powder, mp 139°–142° C.

EXAMPLE 5

Preparation of 3-(4-pyridinylamino)benzonitrile

3-Aminobenzonitrile (11.8 g, 0.10 mol) is added to a solution of 4-chloropyridine hydrochloride (15.0 g, 0.10 mol) in 100 ml of glacial acetic acid. The solution is heated at 100° C. for nine hours, after which time the solution is cooled to room temperature and the acetic acid is removed under vacuum to yield the crude product as an orange oil.

The oil is taken up in 100 ml of water and the resulting solution made basic with 6M sodium hydroxide solution. The resulting hygroscopic solid is collected by filtration and dissolved in 50 ml of acetone. Diethyl ether (50 ml) is added and gaseous hydrogen chloride is bubbled through the solution. The solid which forms is collected by filtration and recrystallized from isopropanol to yield 3-(4-pyridinylamino)benzonitrile as the hydrochloride salt, mp 228°–291° C.

Employing the general synthetic methods described above, the following additional compounds were prepared as described in Table 3.

TABLE 3

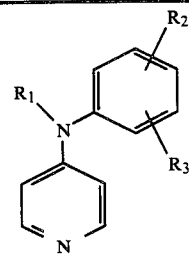

| Example | $R_1$ | $R_2$ | $R_3$ | MP(°C.) |
|---|---|---|---|---|
| 6 | H | H | H | 215–218* |
| 7 | H | H | 4-CH$_3$ | 233–235* |
| 8 | H | H | 3-NO$_2$ | 193–14 197 |
| 9 | H | H | 3-(COOCH$_3$) | 139–142 |
| 10 | H | 3-CH$_3$ | H | 164–168 |
| 11 | H | 4-CH$_3$ | 3-NO$_2$ | >250 |
| 12 | H | 3-OCH$_3$ | H | 203–205* |
| 13 | H | 2-Cl | H | 123–125 |
| 14 | H | 3-Cl | H | 189–190 |
| 15 | H | 3-Cl | H | 165–166* |
| 16 | H | 3-Cl | H | 204–207[1] |
| 17 | H | 3-Cl | H | 150–152[2] |
| 18 | H | 3-Cl | H | 147–149[3] |
| 19 | H | 3-Cl | H | 133–135[4] |

TABLE 3-continued

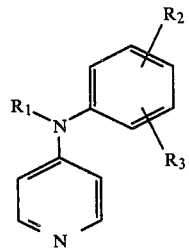

| Example | $R_1$ | $R_2$ | $R_3$ | MP(°C.) |
|---|---|---|---|---|
| 20 | H | 2-Cl | 4-Cl | 195–200 |
| 21 | H | 4-Cl | 3-NO$_2$ | 276–279* |
| 22 | H | 3-CF$_3$ | H | 210–215* |
| 23 | H | 4-CF$_3$ | H | 230–234* |
| 24 | H | 2-NO$_2$ | H | 99–101 |
| 25 | H | 2-NH$_2$ | H | 195–197 |
| 26 | H | 3-NH$_2$ | H | >275* |
| 27 | H | 3-(N(CH$_3$)$_2$) | H | 135–137 |
| 28 | H | 3-(COOC$_2$H$_5$) | H | 110–112 |
| 29 | H | 4-SO$_3$H | H | >275 |
| 30 | —COOCH$_3$ | 3-Cl | 4-Cl | 86–89 |
| 31 | —COOCH$_3$ | H | 4-CH$_3$ | 132–133 |
| 32 | —COCH$_3$ | 3-Cl | 4-Cl | 195–197* |
| 33 | —COCH$_3$ | H | 4-CH$_3$ | >210* |
| 34 | —CO(Phenyl) | 3-Cl | 4-Cl | 131–134 |

*Monohydrochloride salt
[1]Sesquihydrochloride salt
[2]Mononitrate salt
[3]Nitrate salt
[4]Methanesulfonate salt

We claim:

1. A method of treating the symptoms of cognitive decline in an elderly patient comprising adminstering to a patient in need of such treatment an effective amount of a compound having the formula wherein $R_1$ is selected from hydrogen;
alkyl of from one to six carbon atoms;
alkanoyl of from two to six carbon atoms; benzolyl;
—COOH;
—COO—alkyl wherein alkyl contains from one to six carbon atoms;
2-, 3-, or 4-pyridinyl;
phenyl;
phenyl substituted with fluorine, chorine, hydroxy, alkyl of from one to four carbon atoms, or alkoxy of from one to four carbon atoms; or phenylmethyl;
$R_2$ and $R_3$ are independently hydrogen;
alkyl of from one to six carbon atoms;
alkanoyl of from two to six carbon atoms;
carboxyl;
carboxyalkyl in which alkyl contains from one to six carbon atoms;
halogen;

hydroxy;
cyano;
trifluoromethyl;
nitro;
—SO₃H;
amino;
alkylamino or dialkylamino in which alkyl contains from one to four carbon atoms; or a pharmaceutically acceptable salt thereof.

2. A method as defined in claim 1 wherein $R_1$ and $R_2$ are hydrogen, and $R_3$ is as defined therein.

3. A method as defined in claim 1 wherein said compound is N-(3-chlorophenyl)-4-pyridinamine or a pharmaceutically acceptable salt thereof.

4. A method as defined in claim 1 wherein said compound is N-phenyl-4-pyridinamine or a pharmaceutically acceptable salt thereof.

5. A method as defined in claim 1 wherein said compound is N-(3-methylphenyl)-4-pyridinamine or a pharmaceutically acceptable salt thereof.

6. A method as defined in claim 1 wherein said compound is N-(4-methylphenyl)-4-pyridinamine or a pharmaceutically acceptable salt thereof.

7. A method as defined in claim 1 wherein said compound is N-(4-methyl-2-nitrophenyl)-4-pyridinamine or a pharmaceutically acceptable salt thereof.

8. A method as defined in claim 1 wherein said compound is N-(3-methoxyphenyl)-4-pyridinamine or a pharmaceutically acceptable salt thereof.

9. A method is defined in claim 1 wherein said compound is N-(4-methoxyphenyl)-4-pyridinamine or a pharmaceutically acceptable salt thereof.

10. A method as defined in claim 1 wherein said compound is N-(3,4-dimethoxyphenyl)-4-pyridinamine or a pharmaceutically acceptable salt thereof.

11. A method as defined in claim 1 wherein said compound is N-(2-chlorophenyl)-4-pyridinamine or a pharmaceutically acceptable salt thereof.

12. A method as defined in claim 1 wherein said compound is N-(3-chlorophenyl)-4-pyridinamine or a pharmaceutically acceptable salt thereof.

13. A method as defined in claim 1 wherein said compound is N-(2,4-dichlorophenyl)-4-pyridinamine or a pharmaceutically acceptable salt thereof.

14. A method as defined in claim 1 wherein said compound is N-(3,4-dichlorophenyl)-4-pyridinamine or a pharmaceutically acceptable salt thereof.

15. A method as defined in claim 1 wherein said compound is N-(4-chloro-3-nitrophenyl)-4-pyridinamine or a pharmaceutically acceptable salt thereof.

16. A method as defined in claim 1 wherein said compound is N-(2-nitrophenyl)-4-pyridinamine or a pharmaceutically acceptable salt thereof.

17. A method as defined in claim 1 wherein said compound is N-(3-nitrophenyl)-4-pyridinamine or a pharmaceutically acceptable salt thereof.

18. A method as defined in claim 1 wherein said compound is N-4-pyridinyl-1,2-benzenediamine or a pharmaceutically acceptable salt thereof.

19. A method as defined in claim 1 wherein said compound is N-4-pyridinyl-1,3-benzenediamine or a pharmaceutically acceptable salt thereof.

20. A method as defined in claim 1 wherein said compound is N,N-dimethyl-N'-4-pyridinyl-1,3-benzenediamine or a pharmaceutically acceptable salt thereof.

21. A method as defined in claim 1 wherein said compound is N-[3-(trifluoromethyl)phenyl]-4-pyridinamine or a pharmaceutically acceptable salt thereof.

22. A method as defined in claim 1 wherein said compound is N-[4-(trifluoromethyl)phenyl]-4-pyridinamine or a pharmaceutically acceptable salt thereof.

23. A method as defined in claim 1 wherein said compound is 3-(4-pyridinylamino)benzonitrile or a pharmaceutically acceptable salt thereof.

24. A method as defined in claim 1 wherein said compound is 3-(4-pyridinylamino)benzoic acid, methyl ester or a pharmaceutically acceptable salt thereof.

25. A method as defined in claim 1 wherein said compound is 3-(4-pyridinylamino)benzoic acid, ethyl ester or a pharmaceutically acceptable salt thereof.

26. A method as defined in claim 1 wherein said compound is 4-(4-pyridinylamino)benzenesulfonic acid or a pharmaceutically acceptable salt thereof.

27. A method as defined in claim 1 wherein said compound is N-(3,4-dichlorophenyl)-N-4-pyridinyl-4-pyridinamine or a pharmaceutically acceptable salt thereof.

28. A method as defined in claim 1 wherein said compound is N-(3,4-dichlorophenyl)-N-4-pyridinylacetamide or a pharmaceutically acceptable salt thereof.

29. A method as defined in claim 1 wherein said compound is N-(4-methylphenyl)-N-4-pyridinylacetamide or a pharmaceutically acceptable salt thereof.

30. A method as defined in claim 1 wherein said compound is N-(3,4-dichlorophenyl)-N-4-pyridinylbenzamide or a pharmaceutically acceptable salt thereof.

31. A method as defined in claim 1 wherein said compound is (3,4-dichlorophenyl)-4-pyridinylcarbamic acid, methyl ester or a pharmaceutically acceptable salt thereof.

32. A method as defined in claim 1 wherein said compound is (4-methylphenyl)-4-pyridinylcarbamic acid, methyl ester or a pharmaceutically acceptable salt thereof.

33. A method as defined in claim 1 wherein said compound is N-(4-chlorophenyl)-4-pyridinamine or a pharmaceutically acceptable salt thereof.

34. A method as defined in claim 1 wherein said compound is N-(3-chlorophenyl)-N-methyl-4-pyridinamine or a pharmaceutically acceptable salt thereof.

35. A method as defined in claim 1 wherein said compound is N-(4-chlorophenyl)-N-methyl-4-pyridinamine or a pharmaceutically acceptable salt thereof.

* * * * *